(12) United States Patent
Gobbi Frattini

(10) Patent No.: US 9,227,048 B2
(45) Date of Patent: Jan. 5, 2016

(54) HERMETIC CONNECTOR, PIERCEABLE WITHOUT NEEDLE AND AUTOMATICALLY AND SEALINGLY RECLOSABLE, FOR DEVICES INTENDED FOR COLLECTING AND DISPENSING LIQUID SOLUTIONS FOR PHARMACEUTICAL AND/OR NUTRITIONAL USE

(75) Inventor: Paolo Giuseppe Gobbi Frattini, Sondalo (IT)

(73) Assignee: GOBBI FRATTINI, DITTA PAOLO GIUSEPPE, Sondalo So (IT)

( * ) Notice: Subject to any disclaimer, the term of this patent is extended or adjusted under 35 U.S.C. 154(b) by 194 days.

(21) Appl. No.: 13/981,334

(22) PCT Filed: Jan. 24, 2012

(86) PCT No.: PCT/EP2012/051008
§ 371 (c)(1),
(2), (4) Date: Jul. 24, 2013

(87) PCT Pub. No.: WO2012/101101
PCT Pub. Date: Aug. 2, 2012

(65) Prior Publication Data
US 2013/0299021 A1 Nov. 14, 2013

(30) Foreign Application Priority Data
Jan. 28, 2011 (IT) .............................. MI2011A0101

(51) Int. Cl.
*A61M 39/24* (2006.01)
*A61M 39/04* (2006.01)
*A61J 1/14* (2006.01)
*B65D 47/20* (2006.01)
*A61J 1/10* (2006.01)
*A61J 1/20* (2006.01)
*A61M 39/00* (2006.01)

(52) U.S. Cl.
CPC .............. *A61M 39/24* (2013.01); *A61J 1/1406* (2013.01); *A61J 1/1475* (2013.01); *A61M 39/045* (2013.01); *B65D 47/2031* (2013.01);

(Continued)

(58) Field of Classification Search
CPC .............. A61M 39/24; A61M 39/045; A61M 2039/0072; B65D 47/2031; A61J 1/1406; A61J 1/1475; A61J 1/10; A61J 2001/1487; A61J 1/2096; A61J 1/1418; A61J 1/1487; Y10T 137/86485
USPC ........ 251/149.1; 128/912; 604/256, 533, 539, 604/411, 905
See application file for complete search history.

(56) References Cited

U.S. PATENT DOCUMENTS 4,240,411 A * 12/1980 Hosono .......................... 600/154
4,387,879 A * 6/1983 Tauschinski ............... 251/149.1

(Continued)

FOREIGN PATENT DOCUMENTS

WO WO 95/15194 6/1995

*Primary Examiner* — John Bastianelli
(74) *Attorney, Agent, or Firm* — Jacobson Holman, PLLC.

(57) ABSTRACT

A connector for devices intended to collect and dispense liquid solutions for pharmaceutical and/or nutritional use is described. The connector comprises a closing plug pierceable by pressing a needleless introduction/collection tang. The closing plug comprises a check valve with closing lips openable by introducing said tang and elastically reclosable after extracting the introduced tang and further comprising a pierceable and elastically sealingly reclosable membrane placed to hermetically close the inlet end of said check valve. Said closing lips are located at one end of an elastically deformable plastic material body, which is longitudinally crossed by a thin rectangular section slot, the slot being closed on the other end by said pierceable and elastically reclosable membrane.

16 Claims, 4 Drawing Sheets

(52) U.S. Cl.
CPC ............... *A61J 1/10* (2013.01); *A61J 1/1418* (2015.05); *A61J 1/1487* (2015.05); *A61J 1/2096* (2013.01); *A61M 2039/0072* (2013.01); *Y10T 137/86485* (2015.04)

(56) References Cited

U.S. PATENT DOCUMENTS

| | | | | |
|---|---|---|---|---|
| 5,071,551 | A | * | 12/1991 | Muramatsu et al. .......... 210/266 |
| 5,114,408 | A | * | 5/1992 | Fleischhaker et al. ... 604/167.04 |
| 5,158,554 | A | * | 10/1992 | Jepson et al. ................. 604/539 |
| 5,269,771 | A | * | 12/1993 | Thomas et al. ............... 604/539 |
| 5,295,658 | A | * | 3/1994 | Atkinson et al. ........... 251/149.1 |
| 5,336,192 | A | * | 8/1994 | Palestrant ................ 604/167.04 |
| 6,344,033 | B1 | * | 2/2002 | Jepson et al. ................. 604/256 |
| 6,908,459 | B2 | * | 6/2005 | Harding et al. ............... 604/533 |
| 7,025,744 | B2 | * | 4/2006 | Utterberg et al. ............... 604/83 |
| 2002/0172780 | A1 | * | 11/2002 | Halverson ..................... 427/569 |
| 2008/0093571 | A1 | | 4/2008 | Desecki |

\* cited by examiner

HERMETIC CONNECTOR, PIERCEABLE WITHOUT NEEDLE AND AUTOMATICALLY AND SEALINGLY RECLOSABLE, FOR DEVICES INTENDED FOR COLLECTING AND DISPENSING LIQUID SOLUTIONS FOR PHARMACEUTICAL AND/OR NUTRITIONAL USE

This is a national stage of PCT/EP12/051008 filed Jan. 24, 2012 and published in English, which has a priority of Italian no. MI2011A000101 filed Jan. 28, 2011, hereby incorporated by reference.

BACKGROUND OF THE INVENTION

The present invention relates to a hermetic connector, pierceable without needle and automatically and sealingly reclosable, for devices intended for collecting and dispensing liquid solutions for pharmaceutical and/or nutritional use.

BRIEF SUMMARY OF THE INVENTION

In all medical devices intended for dispensing liquid solutions for pharmaceutical and/or nutritional use, the connections between the various parts to be connected for different purposes, such as introduction and collection of liquids, creation of circulation circuits etc., are of fundamental importance.

In particular, containing bags of liquid solutions for pharmaceutical and/or nutritional use, from which flexible tubes usable for introducing additional substances and/or for collecting the solution contained in the bag extend, are known.

Such flexible tubes are closed by hermetically sealed connectors, which should additionally be pierceable for introduction and collection purposes and then hermetically reclosable at the end of the operation.

In particular, connectors for the aforesaid use which comprise a thermoplastic body are known, which connectors can be pierced with the needle of a syringe.

Connectors which do not require a needle because they are closed by a plastic body which can slide in a closing body to establish the communication between a syringe attachment (Luer lock) or the like and the inside of the flexible tube are also known.

Finally, connectors openable without needle are known, for example from US 2008/093571, WO 95/15194 and U.S. Pat. No. 5,268,771, which connectors are provided with a closing plug formed by a deformable plastic body, longitudinally crossed by a slot in which a syringe luer is insertable to determine the provisional opening of an elastically deformable non return valve, which then closes automatically when the luer retracts after the introduction or collection operation.

All these known solutions have problems which include, respectively, the need for a syringe with needle, which may lead to accidental injuries, the lack of hermetic closing before use, the imperfect sealed closing after the first opening operation, the relatively high cost, and more.

In view of the prior art, the present invention has the purpose of making a connector which starting from a hermetic closing state may be pierced without a needle to execute an operation for introducing and collecting the liquid and which may then sealingly reclose after the end of the operation.

The present invention allows to reach such an object by means of a closing plug pierceable by pressing a needleless introduction/collection tang (such as the luer of a syringe), wherein the closing plug comprises a non-return valve with closing lips openable by introducing said tang and elastically reclosable after extracting the introduced tang, characterized in that said closing plug further comprises a pierceable and elastically sealingly closable membrane placed to hermetically close the inlet end of said non-return valve.

By virtue of the present invention, important advantageous effects are obtained, such as the hermetic closing before use, the sealed safety reclosing after each introduction and extraction operation of the introduction/collection tang, the elimination of any back flow effect when the tang is extracted, the low cost, the absence of a needle.

An embodiment of the present invention is shown by way of non-limiting example in the appended drawings, wherein:

DETAILED DESCRIPTION OF THE INVENTION

Figure 1:
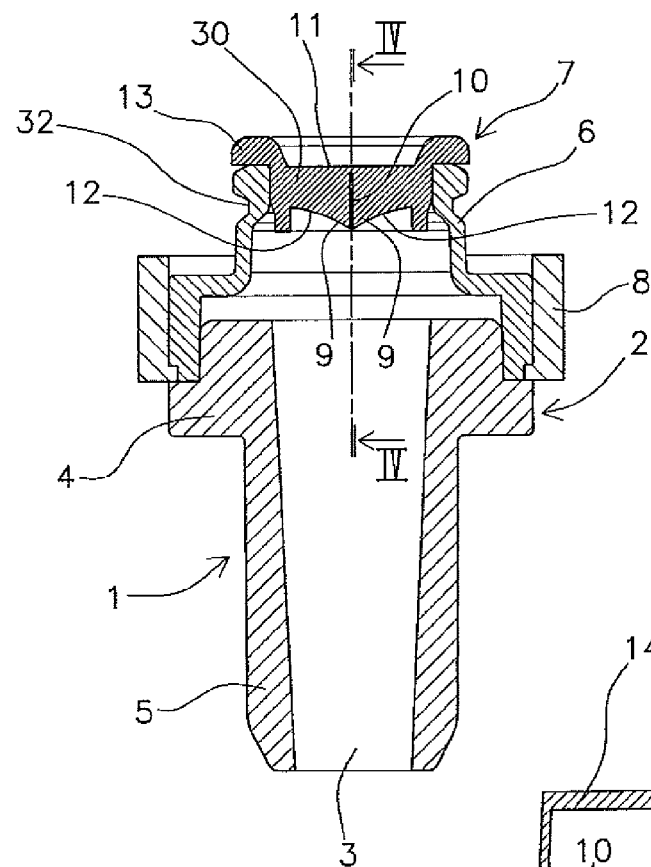
FIG. 1 shows a connector according to the invention in axial section.
Figure 4:
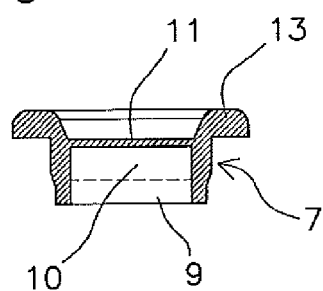
FIG. 4 shows said closing plug in a section view taken along line IV-IV in FIG. 1.

The connector shown in FIGS. 1-4, which is indicated as a whole with numeral 1, comprises a main body 2, preferably made of polypropylene or polycarbonate crossed by an axial hole 3. The main body 2 consists of a collar 4 and an axial extension 5.

A polypropylene or polycarbonate support 6 is fixed to the collar 4 for a closing plug 7 made of elastically deformable plastic material, in particular Thermoplastic Elastomer (TPE), polyisoprene or silicone, and an annular band 8 is arranged and fixed about the support 6.

The closing plug 7 includes a body 30 and a pair of gradually thinner side lips 9 between which a thin rectangular section slot 10 is made, preferably during the step of molding, which slot is open on the lower end and terminates on the top immediately before a thin hermetic closing membrane 11 made in one piece with the rest of the plug 7.

It is worth noting that the sum of the length of the slot (10) and of the thickness of the membrane (11) is shorter than the length of a syringe luer.

The two side lips 9 include concave external recesses 12, which extend laterally from the lower end of the same, starting from the slot 10. An upper collar 13 rests on the top of the support 6.

Figure 5:
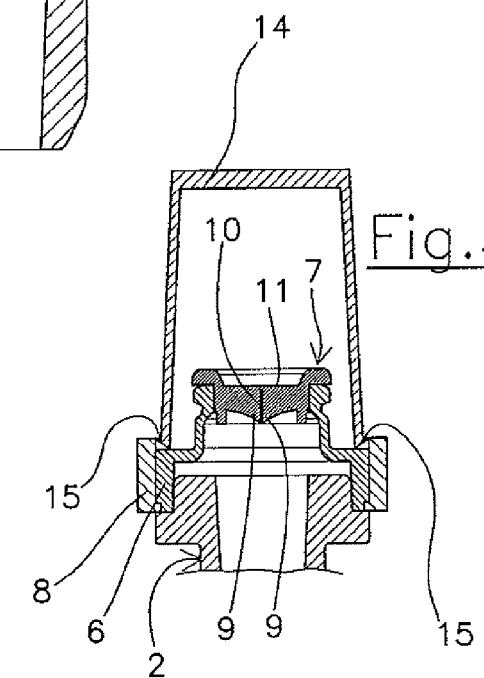
FIG. 5 shows the inlet end of the connector in axial section completed with a protective removable cap.
Figure 2:
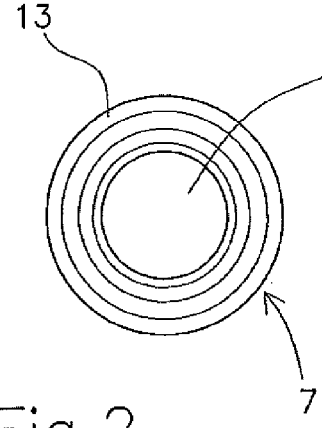
FIG. 2 shows the closing plug of said connector seen from the top with respect to FIG. 1.
Figure 3:
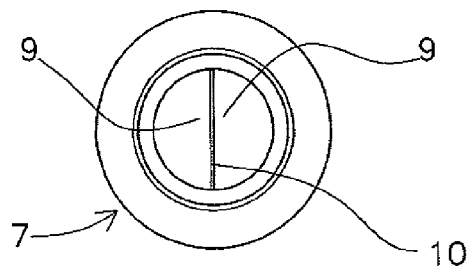
FIG. 3 shows said closing plug seen from the bottom with respect to FIG. 1.

If required, a protective plug 14 overhangs the support 6 and the closing plug 7, as shown in FIG. 5. Easily breakable attachment points 15 hold the cap 14 in position inside the annular band 8 before the first use of the connector 1.

The materials of its components are appropriately subjected to antimicrobic treatment in consideration of the expected use of the connector. In particular, the use of silver ions may be provided, which bind to the cellular wall and penetrate through the same, obstructing the duplication of cell DNA and inhibiting microbe respiration. Alternatively, the use of ionic plasma may be provided.

Figures 6, 7:
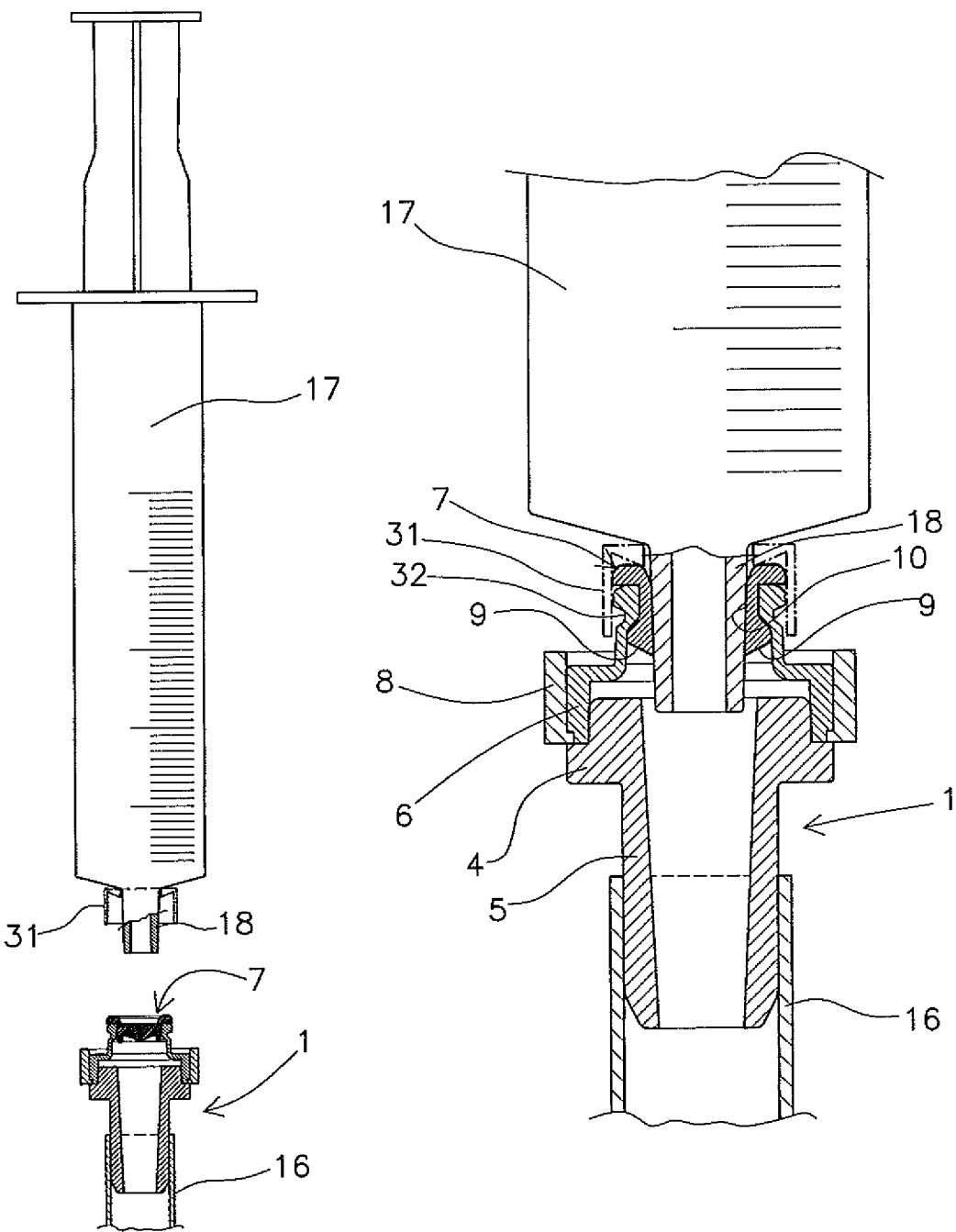
FIG. 6 shows a connector like the one in FIG. 1 and a syringe before their connector for perforating the closing plug of the connector.
FIG. 7 shows in enlarged scale the connector and the syringe after connecting.

FIG. 6 shows a container 1 as the one in FIGS. 1-4, free of the cap 14 and with the axial extension 5 engaged in a flexible tube 16 for introducing or collecting liquid into or from a containing device of the same. In such a condition, the membrane 11 hermetically closes the plug 7, preventing any entrance or exiting of liquid through the axial hole 3. A syringe 17 with luer or connection tang 18 is ready for connecting to the tube 16 by means of the connector 1.

The connection is carried out pressing the luer 18 against the top of the closing plug 7. In this manner, the luer 18 perforates the membrane 11 and is inserted in the slot 10, moving away the two side lips 9 to reach the inlet of the axial hole 3, as shown in FIG. 7.

Since, as mentioned, the overall axial height of the slot 10 and of the membrane 11 is shorter than the length of the luer of a syringe, the luer 18 thus introduced allows the syringe 16 to operate in two-way manner thus allowing the introduction and the collection of liquid through the flexible tube 16.

The syringe may also be of the type known as "Luer lock", i.e. with male luer partially surrounded by an internally threaded coaxial external socket (indicated with a dashed line and with number 31 in FIG. 6). In this case, the insertion of the luer 18 occurs by screwing the external sleeve 31 of the syringe onto the support 6 of the plug 7, exploiting an external groove 32 of the support 6 for such purpose (FIG. 7).

Figure 8:
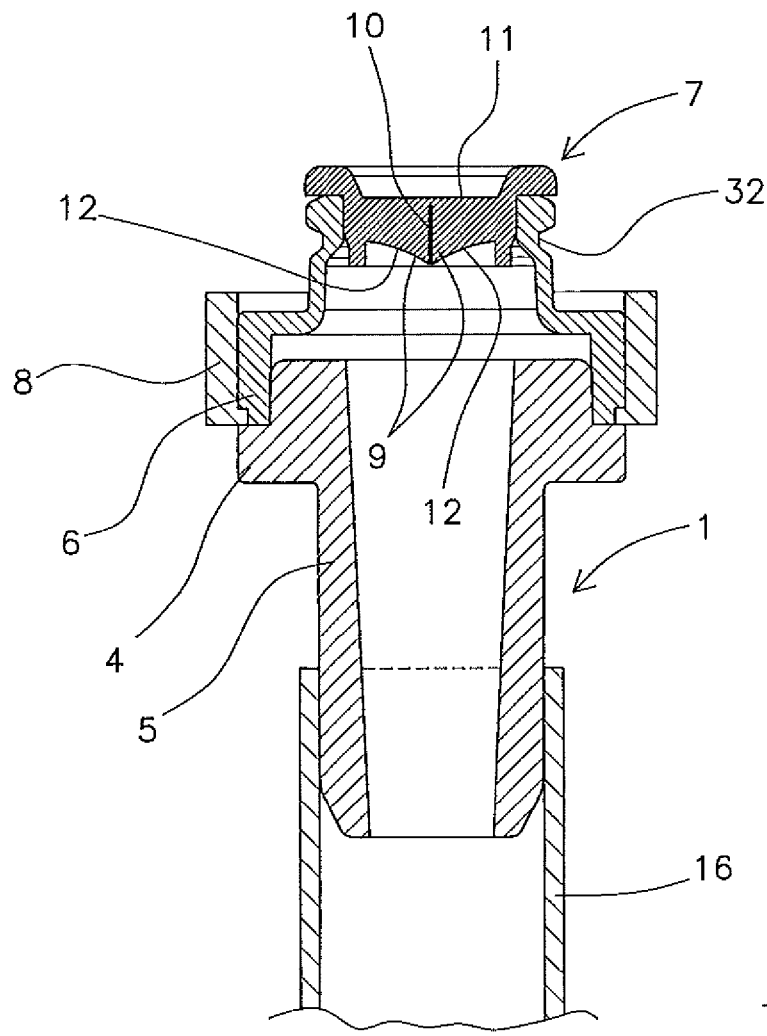
FIG. 8 shows an axial section of the same connector after the disconnection of the syringe.
Figure 9:
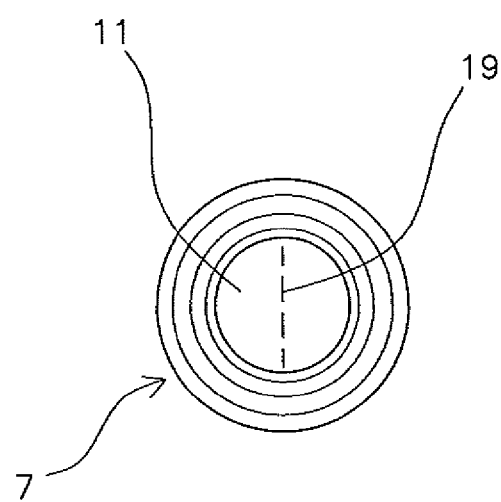
FIG. 9 shows the connector in FIG. 8 in a top plan view.

At the end of the operation, the luer 18 of the syringe may be extracted from the slot 10 of the closing plug 7, the side lips 9 of which close by elastic stress, reaching the position in FIG. 8, identical to the original position in FIG. 1. The membrane 11 also closes elastically, thus obtaining again the hermetic closing of the connector, as shown in FIG. 9, where the dashed-and-dotted line 19 symbolizes the recontact and closing point of the membrane.

The concave shape of the external recesses 12 of the side lips 9 facilitates and forces the closing of the slot 10 and of the membrane 11, thus obtaining the function of non-return valve which prevents the existing of liquid from the flexible tube 16 during and after the extraction of the luer.

Figure 10:
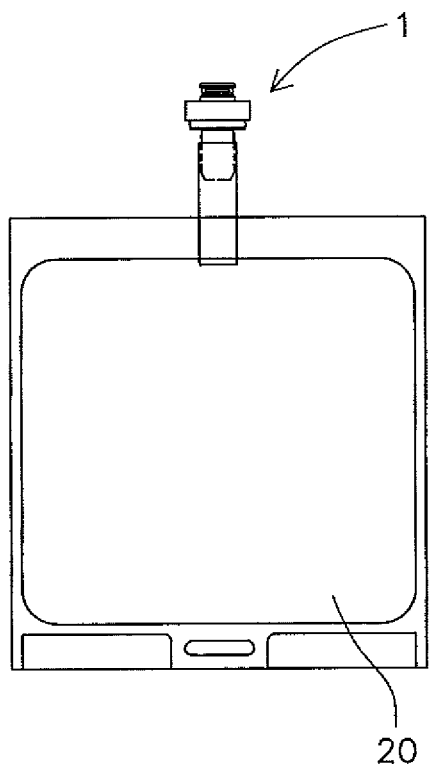
FIGS. 10-13 show some methods of use of the connector according to the invention.
Figure 11:
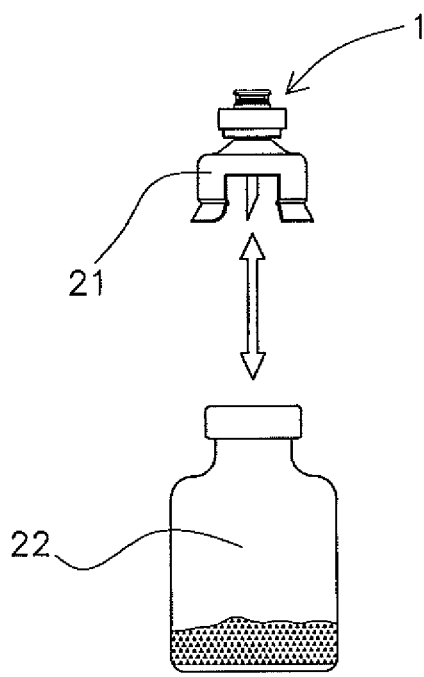
Figure 12:
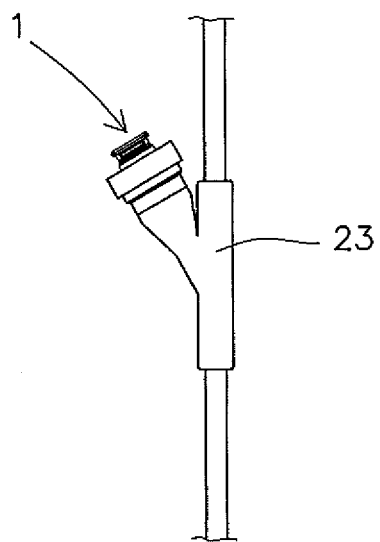
Figure 13:
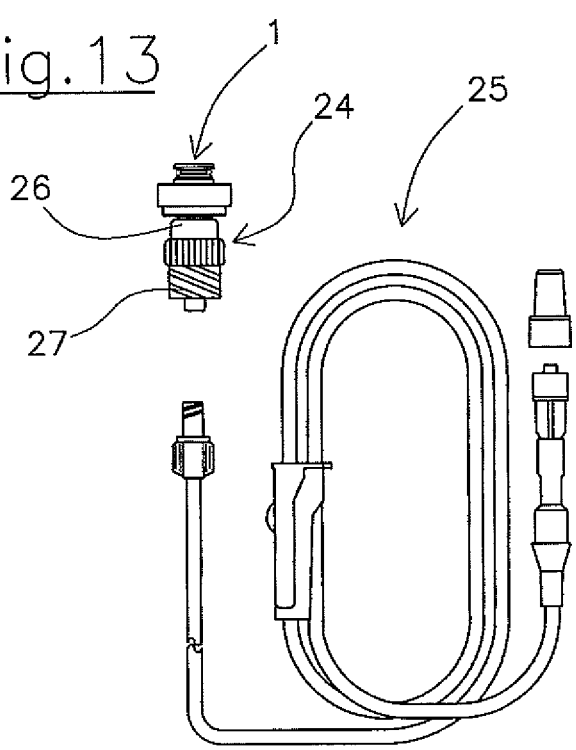

FIGS. 10-13 show methods of use of the connector according to the invention. In particular, FIG. 10 shows its application to a flexible introduction/collection tube of a flexible bag 20 for containing liquid pharmaceutical and/or nutritional solutions and FIG. 11 shows the combination thereof with a fitting 21 for attaching the closing head of a vial 22 for liquid solutions or powders. FIG. 12 shows the association of a connector according to the invention to an infusion tubing 23 with side attachment and FIG. 13 shows the association thereof to a fitting 24 for infusion devices 25 of various types.

It is worth noting that the fitting 24 is of the type described in EP 1 004 329, i.e. made in two parts 26 and 27 rotational with respect to each other to allow the screw fixing of the fitting to the infusion device 25 without needing to turn the part intended for the insertion of the luer of the syringe.

The invention claimed is:

1. A connector for devices intended for collecting and dispensing liquid solutions for pharmaceutical and/or nutritional use, comprising a closing plug pierceable by pressing a needless introduction/collection tang, wherein the closing plug comprises a non-return valve with closing lips openable by introducing said tang and elastically reclosable after extracting the introduced tang, wherein said closing plug is formed by a single body of elastically deformable material which is partially passed through longitudinally by a thin rectangular-section central slot, which is open at a lower end to form said closing lips and is closed at an upper end by a pierceable and elastically sealingly reclosable thin membrane made in one piece with said single body, wherein a lower face of the single body is provided with concave recesses which extend laterally with increasing concavity from the lower end of said closing lips to a lateral downwardly extended collar of the single body.

2. The connector according to claim 1, wherein the sum of the length of said slot and of the thickness of said membrane is shorter than the length of a syringe luer.

3. The connector according to claim 1, wherein said membrane is made by moulding in one piece with said elastically deformable plastic material body and said slot is formed during molding of said one piece.

4. The connector according to claim 1, wherein said elastically deformable plastic material body is made of Thermo Plastic Elastomer (TPE) or polyisoprene or silicone.

5. The connector according to claim 1, wherein said body made of elastically deformable plastic material is located inside a support fixed to a main body crossed by an axial hole.

6. The connector according to claim 5, wherein said support is provided with an external groove suited for screwing the external end socket of a luer type syringe.

7. A connector according to claim 5, wherein said main body has an axial extension suited for inserting a flexible tube for introducing or collecting a liquid in or from a containing device.

8. The connector according to claim 5, wherein a cap is superimposed and connected by easy breakage points to said main body for protecting said closing plug before the first use of the connector.

9. The connector according to claim 5, wherein said support and said main body are made of polypropylene or polycarbonate.

10. The connector according to claim 1, wherein all its components are subjected to antimicrobic treatment.

11. The connector according to claim 10, wherein said antimicrobic treatment is silver ion based.

12. The connector according to claim 10, wherein antimicrobic treatment is carried out with ionic plasma.

13. The connector according to claim 1, which is applied to a flexible tube for introducing and collecting into and from a flexible bag for containing a liquid solution for pharmaceutical and/or nutritional use.

14. The connector according to claim 1, which is applied to a fitting suited for attaching the closing head of a vial for liquid solutions or powders.

15. The connector according to claim 1, which is applied to a line with side attachment.

16. The connector according to claim 1, which is applied to a fitting for lines of various types, wherein said fitting is made in two parts rotational with respect to each other.

* * * * *